United States Patent [19]

Fiorenza et al.

[11] Patent Number: 6,135,967
[45] Date of Patent: Oct. 24, 2000

[54] RESPIRATORY VENTILATOR WITH AUTOMATIC FLOW CALIBRATION

[76] Inventors: Anthony Joseph Fiorenza, 4903 Cactus Ct., Alta Loma, Calif. 91737; John Judson MacDonald, 73-890 Masson St., Palm Desert, Calif. 92260

[21] Appl. No.: 09/299,780

[22] Filed: Apr. 26, 1999

[51] Int. Cl.[7] .................................................. A61B 5/08
[52] U.S. Cl. .................... 600/529; 600/538; 128/200.24; 128/204.21; 128/204.26
[58] Field of Search ................................... 600/529, 538, 600/543; 128/200.24, 204.21, 204.26

[56] References Cited

U.S. PATENT DOCUMENTS

| Re. 29,778 | 9/1978 | Stewart | 128/145.8 |
|---|---|---|---|
| 1,793,226 | 2/1931 | Eggleston et al. | |
| 2,503,563 | 4/1950 | Ray | 137/139 |
| 2,536,691 | 1/1951 | Miller et al. | 137/144 |
| 2,586,677 | 2/1952 | Marrett | 128/188 |
| 2,770,231 | 11/1956 | Falk | 128/29 |
| 2,770,232 | 11/1956 | Falk | 128/29 |
| 2,880,719 | 4/1959 | Andreasen | 128/29 |
| 2,892,348 | 6/1959 | Ekstrom, Jr. | 73/228 |
| 2,904,035 | 9/1959 | Andreasen | 128/29 |
| 3,007,490 | 11/1961 | Passmore | 137/599 |
| 3,015,963 | 1/1962 | Terry | 74/44 |

(List continued on next page.)

FOREIGN PATENT DOCUMENTS

| 2558935 | 7/1977 | Germany | 73/861.53 |
|---|---|---|---|
| 2126666 | 3/1984 | United Kingdom | F04B 21/02 |
| 2166360 | 5/1986 | United Kingdom | A61M 16/01 |
| PCT/US82/ 00795 | 6/1982 | WIPO | A61B 5/08 |
| PCT/FR93/ 00547 | 12/1993 | WIPO . | |

OTHER PUBLICATIONS

"Marks' Standard Handbook for Mechanical Engineers", 8th Edition, Measurement of Fluid Flow Rate, pp. 16–14 through 16–18.

Westlake Plastics, Co., "Thermalux Polysulfone", 1 page.
"Sandvik 11R51 Stainless Thin Strip", Thin Strip with a Smooth Finish, Good Shape and High Fatigue Strength, 4 pages.
"Microprocessor Control of Step Motors", Chapter 15, by S. H. Pollack, Step Motors and Control Systems, pp. 391–402, 1979.
"Electric Motors & Control Techniques", by Irving M. Gottlieb, Stepper Motor Controller, pp. 183–198 and index, 1982.
"Step Motors and Control Systems", Edited by Benjamin C. Kuo, "Drive Circuitry For Step Motors", pp. 114–143 and index, Chapter 4, 1979.
"Stepping Motors and Their Microprocessor Controls", by Takashi Kenjo, "Drive System and Circuitry For Open–Loop Control of Stepping Motors", pp. 121–165 (Chapter 5) 1984.
"Servo Ventilator 900B—Service Manual", by Siemens–Elema, 55 pages plus front and back matter, 1979.
Computer printouts containing abstracts of 62 pages.

*Primary Examiner*—Cary O'Connor
*Assistant Examiner*—Ryan Carter
*Attorney, Agent, or Firm*—Stetina Brunda Garred & Brucker

[57] ABSTRACT

A respiratory ventilator and methodology thereof for automatically calibrating respiration gas flow delivery. The ventilator includes a gas flow calibration member having a reader component for recording inspiratory and exhalation gas volume with exhalation time, and for measuring a plurality of incremental exhalation gas flow values in a plurality of incremental time periods during a single exhalation. The gas flow calibration member includes a composite calculator component for determining an average of consecutive composite flow values, and a scanner calculator component for scanning in reverse order the plurality of consecutive composite flow values and calculating a new flow calibration value where a preselected number of consecutive composite flow values fall within a pre-selected flow rate. Thereafter, the gas delivery member is calibrated in accord with the determined new flow calibration value.

12 Claims, 1 Drawing Sheet

U.S. PATENT DOCUMENTS

| | | | |
|---|---|---|---|
| 3,043,302 | 7/1962 | Spears et al. | 128/203 |
| 3,306,570 | 2/1967 | Cooksley | 251/30 |
| 3,351,057 | 11/1967 | Goodyear et al. | 128/188 |
| 3,374,410 | 3/1968 | Cronquist et al. | 318/138 |
| 3,386,458 | 6/1968 | Wasserman et al. | 137/114 |
| 3,403,556 | 10/1968 | Koester | 73/207 |
| 3,416,054 | 12/1968 | Galles | 318/138 |
| 3,450,382 | 6/1969 | Calim | 251/58 |
| 3,488,030 | 1/1970 | Hulme et al. | 251/134 |
| 3,509,895 | 5/1970 | Henneman | 137/81 |
| 3,569,813 | 3/1971 | Clark et al. | 318/569 |
| 3,579,279 | 5/1971 | Inaba et al. | 318/696 |
| 3,586,953 | 6/1971 | Markkamen et al. | 318/685 |
| 3,675,633 | 7/1972 | Nakajima et al. | 123/119 A |
| 3,727,627 | 4/1973 | Bird et al. | 137/100 |
| 3,759,099 | 9/1973 | McGregor | 73/207 |
| 3,795,145 | 3/1974 | Miller | 73/213 |
| 3,813,592 | 5/1974 | Ryberg | 318/696 |
| 3,820,539 | 6/1974 | Ollivier | 128/145.8 |
| 3,839,662 | 10/1974 | N'Gayen Van | 318/160 |
| 3,840,006 | 10/1974 | Buck et al. | 128/145.8 |
| 3,842,828 | 10/1974 | Bird | 128/145.8 |
| 3,896,837 | 7/1975 | Rohling | 137/110 |
| 3,904,174 | 9/1975 | Glese | 251/331 |
| 3,906,792 | 9/1975 | Miller | 73/213 |
| 3,910,112 | 10/1975 | Gerlach | 73/210 |
| 3,961,627 | 6/1976 | Ernst et al. | 128/145.8 |
| 3,964,310 | 6/1976 | Stenberg | 73/207 |
| 3,968,416 | 7/1976 | Leenhouts | 318/696 |
| 3,985,131 | 10/1976 | Buck et al. | 128/145.8 |
| 4,006,634 | 2/1977 | Billette et al. | 73/207 |
| 4,024,447 | 5/1977 | Epstein | 318/696 |
| 4,027,636 | 6/1977 | Yamamoto et al. | 123/119 A |
| 4,031,448 | 6/1977 | Adachi | 318/696 |
| 4,036,221 | 7/1977 | Hillsman et al. | 128/145.6 |
| 4,081,736 | 3/1978 | Leenhouts et al. | 318/696 |
| 4,083,245 | 4/1978 | Osborn | 73/207 |
| 4,087,732 | 5/1978 | Pritchard | 318/696 |
| 4,094,285 | 6/1978 | Oyama et al. | 123/119 A |
| 4,107,594 | 8/1978 | Jacobs | 318/685 |
| 4,112,757 | 9/1978 | Hayward | 73/207 |
| 4,114,601 | 9/1978 | Abels | 128/1 R |
| 4,119,902 | 10/1978 | Newell | 318/696 |
| 4,121,578 | 10/1978 | Torzala | 128/142 R |
| 4,126,818 | 11/1978 | Taylor | 318/46 |
| 4,126,821 | 11/1978 | Cannon | 318/696 |
| 4,153,021 | 5/1979 | Hattori et al. | 123/119 EC |
| 4,158,351 | 6/1979 | Ando et al. | 123/119 A |
| 4,171,697 | 10/1979 | Arion | 128/145.8 |
| 4,176,687 | 12/1979 | Ensign | 137/625.65 |
| 4,177,830 | 12/1979 | Munson | 137/501 |
| 4,181,108 | 1/1980 | Bellicardi | 123/119 EC |
| 4,193,301 | 3/1980 | Ferrentino | 73/207 |
| 4,199,132 | 4/1980 | deMey, II | 251/134 |
| 4,204,536 | 5/1980 | Albarda | 128/204.22 |
| 4,235,105 | 11/1980 | Walters | 73/861.53 |
| 4,256,100 | 3/1981 | Levy et al. | 128/204.21 |
| 4,256,101 | 3/1981 | Ellestad | 128/204.23 |
| 4,266,573 | 5/1981 | Braatz | 137/630.18 |
| 4,281,651 | 8/1981 | Cox | 128/204.23 |
| 4,285,496 | 8/1981 | Coles | 251/130 |
| 4,297,998 | 11/1981 | Christianson | 128/204.26 |
| 4,304,136 | 12/1981 | McCabe et al. | 73/861.54 |
| 4,323,064 | 4/1982 | Hoenig et al. | 128/204.21 |
| 4,326,513 | 4/1982 | Schulz et al. | 128/283.14 |
| 4,328,823 | 5/1982 | Schrieber | 137/204.26 |
| 4,333,453 | 6/1982 | Rodder | 128/205.24 |
| 4,336,590 | 6/1982 | Jacq et al. | 364/418 |
| 4,350,050 | 9/1982 | Nelson | 73/861.54 |
| 4,368,646 | 1/1983 | Rogg | 73/861.55 |
| 4,393,869 | 7/1983 | Boyarsky et al. | 128/204.18 |
| 4,401,116 | 8/1983 | Fry et al. | 128/205.24 |
| 4,421,113 | 12/1983 | Gedeon et al. | 128/204.23 |
| 4,433,685 | 2/1984 | Giorgini et al. | 128/204.26 |
| 4,436,090 | 3/1984 | Darling | 128/204.26 |
| 4,448,192 | 5/1984 | Stawitcke et al. | 128/204.26 |
| 4,457,304 | 7/1984 | Molnar et al. | 128/204.25 |
| 4,457,339 | 7/1984 | Juan et al. | 137/624.16 |
| 4,459,982 | 7/1984 | Fry | 128/204.23 |
| 4,474,068 | 10/1984 | Knetsch et al. | 73/861.53 |
| 4,484,554 | 11/1984 | Nakajima et al. | 123/339 |
| 4,493,614 | 1/1985 | Chu et al. | 417/22 |
| 4,524,804 | 6/1985 | Goedecke et al. | 137/625.64 |
| 4,527,557 | 7/1985 | DeVries et al. | 128/204.23 |
| 4,535,816 | 8/1985 | Feder et al. | 137/625.65 |
| 4,540,018 | 9/1985 | Dantlgraber | 137/540 |
| 4,548,382 | 10/1985 | Otting | 251/5 |
| 4,552,027 | 11/1985 | Larner | 73/861.53 |
| 4,561,408 | 12/1985 | Jenkins | 123/571 |
| 4,570,631 | 2/1986 | Durkan | 128/204.23 |
| 4,576,159 | 3/1986 | Hahn et al. | 128/203.14 |
| 4,579,145 | 4/1986 | Leiber et al. | 137/625.65 |
| 4,587,967 | 5/1986 | Chu et al. | 128/204.21 |
| 4,592,349 | 6/1986 | Bird | 128/204.25 |
| 4,597,387 | 7/1986 | Carnegie et al. | 128/201.27 |
| 4,602,653 | 7/1986 | Ruiz-Vela et al. | 137/88 |
| 4,604,902 | 8/1986 | Sabin et al. | 73/861.04 |
| 4,606,340 | 8/1986 | Ansite | 128/205.24 |
| 4,611,591 | 9/1986 | Inui et al. | 128/205.24 |
| 4,614,122 | 9/1986 | Graves | 73/861.74 |
| 4,617,637 | 10/1986 | Chu et al. | 364/505 |
| 4,619,139 | 10/1986 | Rosaen | 73/198 |
| 4,635,631 | 1/1987 | Izumi | 128/204.23 |
| 4,677,603 | 6/1987 | Kenjyo | 369/32 |
| 4,688,433 | 8/1987 | Silverwater | 73/861.53 |
| 4,699,137 | 10/1987 | Schroeder | 128/205.24 |
| 4,702,240 | 10/1987 | Chaoui | 128/204.18 |
| 4,790,194 | 12/1988 | Bellows et al. | 73/861.53 |
| 4,821,767 | 4/1989 | Jackson | 137/491 |
| 4,838,257 | 6/1989 | Hatch | 128/204.18 |
| 4,840,457 | 6/1989 | Remer | 350/255 |
| 4,854,574 | 8/1989 | Larson et al. | 272/99 |
| 4,898,174 | 2/1990 | Fangrow, Jr. | 128/204.24 |
| 4,957,107 | 9/1990 | Sipin | 128/204.21 |
| 4,966,193 | 10/1990 | De Campos | 137/625.35 |
| 4,993,269 | 2/1991 | Guillaume et al. | 73/861.53 |
| 5,014,694 | 5/1991 | DeVries | 128/205.24 |
| 5,044,362 | 9/1991 | Younes | 128/204.21 |
| 5,072,729 | 12/1991 | DeVries | 128/204.23 |
| 5,099,635 | 3/1992 | Butkovich et al. | 56/13.5 |
| 5,107,830 | 4/1992 | Younes | 128/204.18 |
| 5,127,400 | 7/1992 | DeVries et al. | 128/205.24 |
| 5,148,802 | 9/1992 | Sanders et al. | 128/204.18 |
| 5,159,924 | 11/1992 | Cegielski et al. | 128/203.12 |
| 5,197,895 | 3/1993 | Stupecky | 439/194 |
| 5,239,995 | 8/1993 | Estes et al. | 128/204.23 |
| 5,315,990 | 5/1994 | Mondry | 128/205.11 |

RESPIRATORY VENTILATOR WITH AUTOMATIC FLOW CALIBRATION

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

This invention relates in general to respiratory ventilators, and in particular to a respiratory ventilator having automatic flow calibration of respiratory gas delivered in accord with immediately preceding breath data.

Certain respiratory diseases not only require patient special care with respect to physical activity and attendant exertion levels, but also require specialized mechanical augmentation to permit the patient to simply accomplish the act of breathing. Thus, while lung disfunction, lung tissue degradation, autonomic nervous system disability, etc. can significantly interfere with proper inhalation and exhalation action and thereby deprive an individual of adequate oxygenation and attendant carbon dioxide removal, employment of a ventilator for positive respiratory regulation can result in a highly beneficial contribution toward life quality. As required, and in accord with actual maladies encountered, such ventilator therapy can be administered in association with physical activity-monitoring to thereby provide a treatment program to the patient that achieves improved comfort in day-to-day functions along with medically acceptable respiratory levels.

Ventilators presently in service generally operate under constant parameters that are pre-set such that inhalation and expiration of air or oxygen-enriched air does not automatically vary, but, instead, can be changed manually if a health care provider in charge of a treatment program determines such modification is desired. Therefore, volume, pressure, and delivery duration of inspiratory air or oxygen-enriched air are quantitatively estimated in accord with standard expectations usually present under a majority of circumstances in similarly-situated patients. While these parameters may adequately serve most patients most of the time, any patients whose needs do not fit expectations must endure at least partially ineffective ventilation until manual readjustment of the ventilator can be completed. Further, of course, any momentary change of respiratory needs such as that encountered in momentary exertion for whatever reason is not addressed by a ventilator whose delivery capabilities can be modified only through manual adjustment unless a technician just happens to be present.

In view of these limitations, it is apparent that a need is present for a ventilator apparatus that is more responsive to patient needs. It is therefore a primary object of the present invention to provide a ventilator that is capable of sensing untoward respiratory activity and thereafter responding to such activity.

Another object of the present invention is to provide a ventilator whose respiratory sensor member comparatively monitors incremental exhalation flow parameters during a single exhalation and automatically calibrates ventilator output to maintain or change such output in accord with such exhalation parameters.

Yet another object of the present invention is to provide a ventilator whose calibrateable parameters include volume, pressure, and delivery-duration of air or oxygen-enriched air as administered to a patient.

These and other objects of the present invention will become apparent throughout the description thereof which now follows.

BRIEF SUMMARY OF THE INVENTION

The present invention is a respiratory ventilator for monitoring breath flow and automatically regulating and calibrating respiration gas flow delivery in accord with such monitored breath flow. The ventilator first comprises a respiratory gas delivery member having a calibrateable gas flow adjuster and a calibrateable gas pressure adjuster that regulate delivery of respiratory gas. Second, the ventilator comprises a gas flow calibration member in communication with the gas flow adjuster and gas pressure adjuster for calibrating these adjusters to thereby regulate delivery of respiratory gas. The gas flow calibration member first comprises a reader component for recording inspiratory gas volume, exhalation gas volume, and exhalation time, and for measuring a plurality of incremental exhalation gas flow values in a plurality of incremental time periods during a single exhalation and averaging as a set of consecutive flow values a preselected number of these flow values. Second, the gas flow calibration member comprises a composite calculator component for determining an average composite flow value of a plurality of consecutive sets of flow values and thereafter determining an average aggregate flow value of a plurality of consecutive composite flow values. The composite calculator component additionally determines a volume flow calibration value as the difference between inspired and exhaled gas volume divided by exhalation time. Third, the gas flow calibration member comprises a scanner calculator component for scanning in reverse order the plurality of consecutive composite flow values and calculating a new flow calibration value where a preselected number of consecutive composite flow values fall within a pre-selected flow rate. Thereafter, the gas flow adjuster and gas pressure adjuster are calibrated in accord with the determined new flow calibration value.

In a preferred embodiment, the scanner calculator component calculates a new flow calibration value where 60 consecutive composite flow values fall within a flow rate of ±2.5 liters per minute per millisecond, or where less than 60 consecutive composite flow values fall within a flow rate of ±2.5 liters per minute per millisecond. In the latter event, certain criteria must be met, and include (i) an existing flow calibration value that is greater than an existing bias flow plus 2.5 liters per minute, (ii) a volume flow calibration value that is less than the bias flow plus 2.5 liters per minute, and (iii) the existing flow calibration value minus the volume flow calibration value must be greater than 3.1 liters per minute. When all three qualifying conditions are met, the gas flow adjuster and gas pressure adjuster are calibrated to a flow calibration value equal to the volume flow calibration value minus 1.0 liter per minute.

The present invention additionally includes methodology as exemplified in the operation of the ventilator for sensing untoward respiratory activity and thereafter responding to such activity. Thus, the present ventilator and methodology comparatively monitors incremental exhalation flow parameters during consecutive single exhalations and automatically calibrates ventilator output to maintain or change such output in accord with these exhalation parameters and the thereby reflected needs of a patient.

BRIEF DESCRIPTION OF THE DRAWING

An illustrative and presently preferred embodiment of the invention is shown in the accompanying drawings in which.

DETAILED DESCRIPTION OF THE INVENTION

Figure 1:
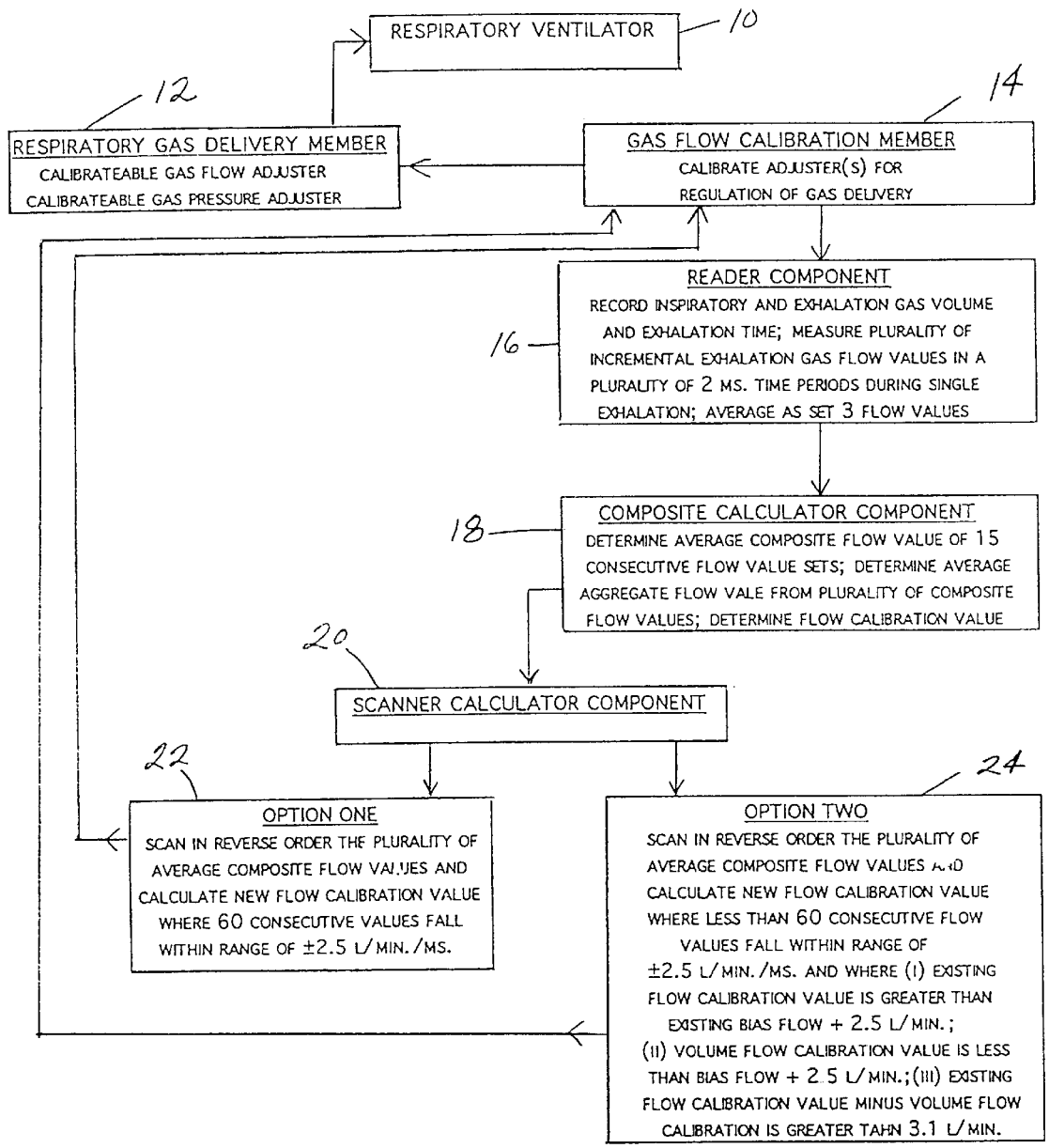
FIG. 1 is a flow chart defining ventilator operation and respiratory gas flow calibration methodology.

Referring to the drawing FIGURE, a respiratory ventilator 10 is conventionally equipped with a respiratory gas delivery member 12 and a gas flow calibration member 14. Gas delivery from the delivery member 12 to a patient is regulated by a standard calibrateable gas flow adjuster and a standard calibrateable gas pressure adjuster to thereby maintain a desired flow, defined throughout this application as the volume of gas per unit of time, of air, oxygen enriched air, or the like, to a patient. The gas flow calibration member 14 has a reader component 16, a composite calculator component 18, and a scanner calculator component 20 all conventionally cooperatively networked such that data is shared among all three components 16, 18, 20. In addition to recording inspiratory and exhalation gas volume of an individual breath along with exhalation time for that breath, the reader component 16 measures a plurality of incremental exhalation gas flow values in a plurality of two millisecond timer periods during breath exhalation, and thereafter averaging a series of three consecutive flow values to produce at least 15 consecutive sets. The composite calculator component 18 then receives the 15 consecutive sets of flow values to first average these values to thereby determine an average composite flow value and to second determine an average aggregate flow value derived from the averaging a plurality of average composite flow values. The composite calculator component 18 additionally determines a volume flow calibration value calculated as the difference between inspired and exhaled gas volume divided by exhalation time.

Data from the composite calculator component 18 is conventionally transmitted to the scanner calculator component 20 where initial scanning is performed in reverse order on the plurality of composite flow values to calculate a new flow calibration value on data under "Option One" 22 where 60 consecutive composite flow values fall within a flow rate of ±2.5 liters per minute per millisecond. Such calibration value is transmitted to the gas flow calibration member 14 for subsequent appropriate calibration of the gas flow and/or gas pressure adjuster(s) of the gas delivery member 12 and ultimate calibrated output from the ventilator 10. When less than 60 consecutive composite flow values fall within a flow rate of ±2.5 liters per minute per millisecond, data from that exhalation is ignored and no new calibration value is calculated unless all of the following are present as defined in "Option Two" 24: (i) the existing flow calibration value is greater than the existing bias flow plus 2.5 liters per minute, (ii) the volume flow calibration value is less than the bias flow plus 2.5 liters per minute, and (iii) the existing flow calibration value minus the volume flow calibration value is greater than 3.1 liters per minute. When all the criteria of (i), (ii), and (iii) are present, a flow calibration value equal to the volume flow calibration value minus 1.0 liter per minute is transmitted to the gas flow calibration member 14 for subsequent appropriate calibration of the gas flow and/or gas pressure adjuster(s) of the gas-delivery member 12 and ultimate calibrated output from the ventilator 10 in the same manner as earlier related.

In operation, all of the described events are performed automatically during every breath. Consequently, a patient whose respiratory maladies are addressed by the ventilator 10 can experience a generally consistent respiratory pattern generally irrespective of extraneous factors that may include nebulizer use, random exertion, altitude changes, and other impinging influences. Additionally, because both gas flow and gas pressure are under consideration for calibration, a proper flow can be delivered to a patient where pressurized force is indicated for sufficient respiratory gas inhalation. The ventilator and operational methodology here described thereby produces a life quality for respiratory disease sufferers.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A respiratory ventilator for monitoring breath flow and automatically regulating and calibrating respiration gas flow delivery in accord with such monitored breath flow, the ventilator comprising:

a) a respiratory gas delivery member having a calibrateable gas flow adjuster and a calibrateable gas pressure adjuster, wherein said flow and pressure adjusters regulate delivery of respiratory gas; and b) a gas flow calibration member in communication with the gas flow adjuster and gas pressure adjuster for calibrating said adjusters to thereby regulate delivery of respiratory gas, said gas flow calibration member comprising:

1) a reader component for recording inspiratory gas volume, exhalation gas volume, and exhalation time of an individual breath, and for measuring a plurality of incremental exhalation gas flow values in a plurality of incremental time periods during exhalation of said individual breath and averaging as a set of consecutive flow values a pre-selected number of said flow values;

2) a composite calculator component for determining an average composite flow value of a plurality of consecutive sets of flow values and thereafter determining and saving an average aggregate flow value of a plurality of consecutive composite flow values, and additionally for determining a volume flow calibration value as the difference between inspired and exhaled gas volume divided by exhalation time; and 3) a scanner calculator component for scanning in reverse order the plurality of consecutive composite flow values and calculating a new flow calibration value where a pre-selected number of consecutive composite flow values fall within a pre-selected flow rate, and thereafter for calibration of the gas flow adjuster and gas pressure adjuster.

2. A respiratory ventilator as claimed in claim 1 wherein each incremental time period is two milliseconds.

3. A respiratory ventilator as claimed in claim 2 wherein the pre-selected number of flow values of each set is determined from three consecutive flow values.

4. A respiratory ventilator as claimed in claim 3 wherein the average composite flow value is determined from 15 consecutive sets.

5. A respiratory ventilator as claimed in claim 4 wherein the pre-selected number of composite flow values for calculating a new flow calibration is 60 and the pre-selected flow rate is ±2.5 liters per minute per millisecond.

6. A respiratory ventilator for monitoring breath flow and automatically regulating and calibrating respiration gas flow delivery in accord with such monitored breath flow, the ventilator comprising:

a) a respiratory gas delivery member having a calibrateable gas flow adjuster and a calibrateable gas pressure adjuster, wherein said flow and pressure adjusters regulate delivery of respiratory gas; and b) a gas flow calibration member in communication with the gas flow adjuster and gas pressure adjuster for calibrating said adjusters to thereby regulate delivery of respiratory gas, said gas flow calibration member comprising:

1) a reader component for recording inspiratory gas volume, exhalation gas volume, and exhalation time of an individual breath, and for measuring a plurality of incremental exhalation gas flow values in a plurality of consecutive two millisecond time periods during exhalation of said individual breath and averaging as a set of flow values three consecutive flow values;

2) a composite calculator component for determining an average composite flow value of 15 consecutive sets of flow values and thereafter determining and saving an average aggregate flow value of a plurality of consecutive composite flow values, and additionally for determining a volume flow calibration value as the difference between inspired and exhaled gas volume divided by exhalation time; and 3) a scanner calculator component for scanning in reverse order the plurality of composite flow values and calculating a new flow calibration value where 60 consecutive composite flow values fall within a flow rate of ±2.5 liters per minute per millisecond or where less than 60 consecutive composite flow values fall within a flow rate of ±2.5 liters per minute per millisecond and wherein (i) an existing flow calibration value is greater than an existing bias flow plus 2.5 liters per minute, (ii) the volume flow calibration value is less than said bias flow plus 2.5 liters per minute, and (iii) said existing flow calibration value minus said volume flow calibration value is greater than 3.1 liters per minute, and thereafter for calibration of the gas flow adjuster and gas pressure adjuster to a flow calibration value equal to said volume flow calibration value minus 1.0 liter per minute.

7. A method for monitoring breath flow and regulating and calibrating respiration gas flow delivery by a ventilator in accord with such monitored breath flow, the method comprising:

a) activating a ventilator comprising a respiratory gas delivery member having a calibrateable gas flow adjuster and a calibrateable gas pressure adjuster, wherein said flow and pressure adjusters regulate delivery of respiratory gas;

b) recording inspiratory gas volume, exhalation gas volume, and exhalation time of an individual breath, and measuring a plurality of incremental exhalation gas flow values in a plurality of incremental time periods during exhalation of said individual breath and averaging as a set of consecutive flow values a pre-selected number of said flow values;

c) determining an average composite flow value of a plurality of consecutive sets of flow values and thereafter determining and saving an average aggregate flow value of a plurality of consecutive composite flow values, and additionally determining a volume flow calibration value as the difference between inspired and exhaled gas volume divided by exhalation time;

d) scanning in reverse order the plurality of consecutive composite flow values and calculating a new flow calibration value where a pre-selected number of consecutive composite flow values fall within a pre-selected flow rate; and e) automatically transmitting the new flow calibration value to the gas flow adjuster and gas pressure adjuster of the ventilator to thereby regulate delivery of respiratory gas.

8. A method for monitoring breath flow and regulating and calibrating respiration gas flow delivery as claimed in claim 7 wherein each incremental time period is two milliseconds.

9. A method for monitoring breath flow and regulating and calibrating respiration gas flow delivery as claimed in claim 8 wherein the pre-selected number of flow values of each set is determined from three consecutive flow values.

10. A method for monitoring breath flow and regulating and calibrating respiration gas flow delivery as claimed in claim 9 wherein the average composite flow value is determined from 15 consecutive sets.

11. A method for monitoring breath flow and regulating and calibrating respiration gas flow delivery as claimed in claim 10 wherein the pre-selected number of composite flow values for calculating a new flow calibration is 60 and the pre-selected flow rate is ±2.5 liters per minute per millisecond.

12. A method for monitoring breath flow and regulating and calibrating respiration gas flow delivery by a ventilator in accord with such monitored breath flow, the method comprising:

a) recording inspiratory gas volume, exhalation gas volume, and exhalation time of an individual breath, and measuring a plurality of incremental exhalation gas flow values in a plurality of consecutive two millisecond time periods during exhalation of said individual breath and averaging as a set of flow values three consecutive flow values;

2) determining an average composite flow value of 15 consecutive sets of flow values and thereafter determining and saving an average aggregate flow value of a plurality of consecutive composite flow values, and additionally determining a volume flow calibration value as the difference between inspired and exhaled gas volume divided by exhalation time; and 3) scanning in reverse order the plurality of composite flow values and calculating a new flow calibration value where 60 consecutive composite flow values fall within a flow rate of ±2.5 liters per minute per millisecond or where less than 60 consecutive composite flow values fall within a flow rate of ±2.5 liters per minute per millisecond and wherein (i) an existing flow calibration value is greater than an existing bias flow plus 2.5 liters per minute, (ii) the volume flow calibration value is less than said bias flow plus 2.5 liters per minute, and (iii) said existing flow calibration value minus said volume flow calibration value is greater than 3.1 liters per minute, and thereafter calibrating a gas flow adjuster and gas pressure adjuster of the ventilator to a flow calibration value equal to said volume flow calibration value minus 1.0 liter per minute.

* * * * *